United States Patent [19]

Jones

[11] Patent Number: 4,951,689

[45] Date of Patent: Aug. 28, 1990

[54] ARMORING SYSTEM FOR PROTECTIVE BODY COVERS

[76] Inventor: J. Paul Jones, 413 N. Saddlebrook Cir., Chester Springs, Pa. 19425

[21] Appl. No.: 207,867

[22] Filed: Jun. 17, 1988

[51] Int. Cl.$^5$ .................. A61F 13/00; F41H 1/02; A41D 19/00
[52] U.S. Cl. .................................. 128/878; 2/25; 2/160; 2/161 R
[58] Field of Search .............. 128/878, 879, 880, 157, 128/165, 889, 892; 2/2.5, 1, 159, 161 R, 69, 160

[56] References Cited

U.S. PATENT DOCUMENTS

| | | | |
|---|---|---|---|
| 19,018 | 1/1858 | Cohen | 2/161 R |
| 192,082 | 6/1877 | Peters | 2/161 R |
| 921,352 | 5/1905 | Blaker | 2/2.5 |
| 1,021,804 | 4/1912 | Schneider | 2/2.5 |
| 1,268,223 | 6/1918 | Elmer | 2/2.5 |
| 1,269,930 | 6/1918 | Hawley | 2/2.5 |
| 1,282,411 | 10/1918 | Golembiowski | 2/2.5 |
| 1,929,318 | 10/1933 | Klosky | 128/880 |
| 1,990,384 | 2/1935 | Klohs | 128/880 |
| 2,742,898 | 4/1956 | Beaudry | 128/880 |
| 2,895,139 | 7/1959 | Compton | 2/161 R |
| 3,084,686 | 4/1963 | Perconti | 128/879 |
| 3,236,553 | 2/1966 | Shrier | 2/161 R |
| 4,107,840 | 8/1978 | Kupperman | 2/161 R |
| 4,766,914 | 8/1988 | Briggs | 2/159 |

Primary Examiner—Robert A. Hafer
Assistant Examiner—Michael Brown

[57] ABSTRACT

A system for providing metallic armor protection for flexible body covers, such as gloves or finger cots, to prevent accidental cutting or piercing of the wearer by sharp instruments, such as scalpels or hypodermic needles.

The flexible elastomer material that is used for the protective cover is provided with small closely spaced projections, on which overlapping circular metal discs are impaled. The overlapping metallic discs are free to move over each other to allow total flexibility; and the small round ended elastomer projections provide excellent friction to grasp smooth metallic objects, and transmit the sense of touch.

2 Claims, 3 Drawing Sheets

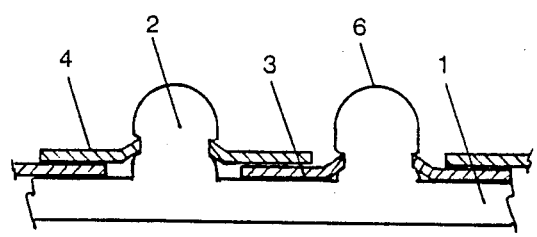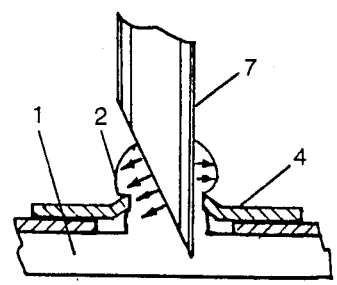
FIG. 1A
FIG. 2
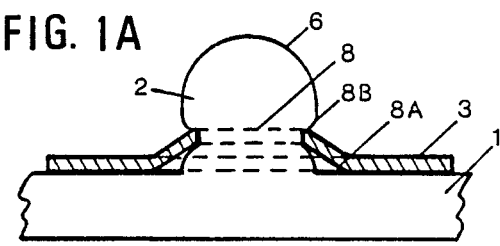
FIG. 1B
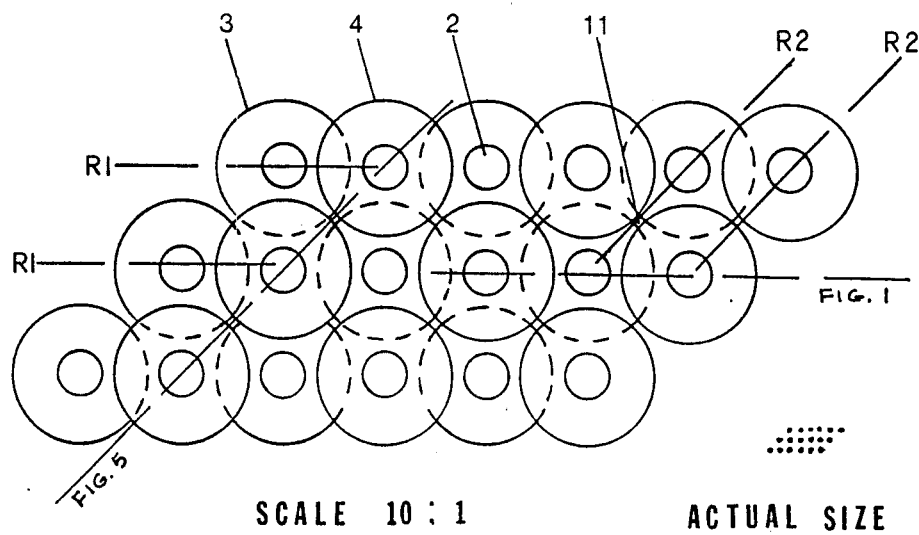
SCALE 10 : 1     ACTUAL SIZE
FIG. 3A     FIG. 3B

ARMORING SYSTEM FOR PROTECTIVE BODY COVERS

BACKGROUND

It has been estimated by the Biochemical Business International organization that there are close to one million accidental hypodermic needle sticks or scalpel cuts per year among health care workers and surgeons. The Occupational Safety and Health Administration estimates that at least 300 health care workers die annually from accidental Hepatitis B infections and complications. Now, the added possibility of contracting lethal blood transferred diseases, such as AIDS, has made the need for new protective methods for the health care workers imperative.

For the surgeons who can be directly exposed to contaminated blood by accidental scalpel cuts during operations, a company is now providing metal chain mesh glove covers. Although this chain mail armor approach can prevent scalpel cuts, it is at the obvious expense of manual dexterity, and the necessary friction to hold smooth metal instruments. In addition to the loss of touch sensitivity, this type of armor is not impervious to hypodermic needle pricks. The metal mesh gloves are also quite heavy for long term usage, and they are very expensive because of the labor intensive process of manufacture.

It is, therefore, one object of this invention to provide an armoring method for rubber gloves and similar covers, which has the armor elements as an integral part of the basic protective cover, with a minimum addition of weight, or loss of flexibility.

It is another object of this invention to provide an armoring method which, when used on elastomer finger covers, will not cause any appreciable loss of touch sensitivity, or loss of gripping friction.

It is yet another object of this invention to provide an armoring method for elastomer protective products, that is adaptable to automatic machine assembly, with the potential of making the product available on the massive scale that is required to solve the aforementioned serious problems in the health care field.

FIG. 1A shows a cross sectional view through a row of projections from a base sheet of elastomer material. The projections are retaining metal discs at alternating levels, while also extending above the metal disc surfaces, to provide friction to the object that is being contacted.

FIG. 1B also shows a detail of the mounting hole in an individual metal disc, with the bottom conic entry and the sharp edge on top to impale the elastomer projection.

FIG. 2 shows a hypodermic needle attempting to pass thru the center aperture of an armor disc.

FIGS. 3A and 3B show a plan view of a section of the armored base material, looking straight in on the round ends of the retaining projections. Every other row has metal discs at one level; and each alternate row has similar discs at a second overlapping level. FIG. 3B shows the projections only; actual size.

Figure 4:
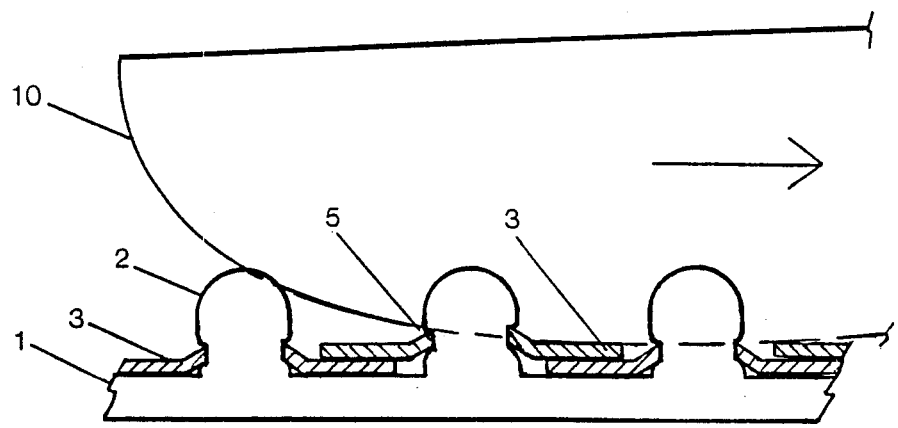
FIG. 4 shows how the metal discs form a metal shield to the cutting edge of a scalpel blade, even though individual elastomer projections may be cut during an accidental slip of the scalpel; as shown.
Figure 5:
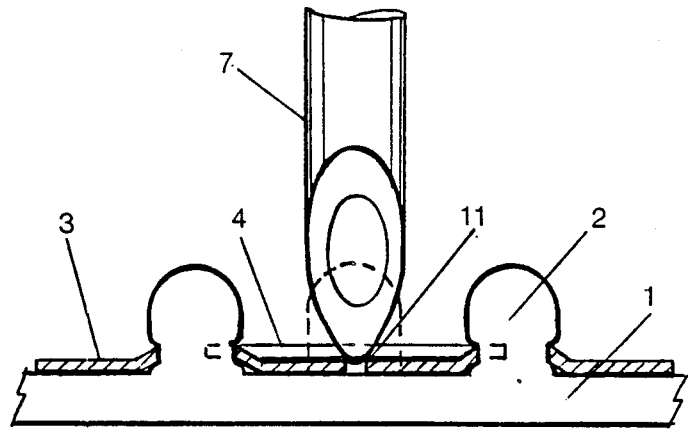
FIG. 5 shows the compliance or tolerance provided in the assembly of the discs, which allows complete flexibility of the armored material, but will still not permit entry of a typical hypodermic needle at the intersection of the discs.

Additional features of the Armoring System invention, and the inherent methods of manufacture, will be more clearly defined in the following description:

DESIGN FEATURES

The basic elements of the armoring system, regardless of the type cover that is being protected, is shown in FIG. 1. Since armoring of sterile gloves for the surgeon would be one of the most demanding requirements, the description will be limited to the particular needs of the surgeon; and how the armoring system will protect the surgeons fingers from scalpel cuts and hypodermic "sticks"; while not hampering their manual dexterity.

With reference to FIG. 1A, the sheet elastomer Base 1 can represent a form-fitting surgeons glove, which can have a thickness of 0.010 to 0.020 inch rubber. The round ended Projections 2 are approximately 0.032 inch in diameter and 0.032 inch high, and are spaced on a grid that is, in proportion, 0.070 inch square. The typical Armor Disc 3 or 4 is 0.093 inch in diameter, and has a center hole that is 0.026 inch in diameter; and is approximately 0.003 to 0.004 inches thick. With reference to FIG. 1A, the Round Ends 6 on the Projections 2, and the conic edge 8A of the center Aperture 8, allow the Discs 4 to be forced on to the Projections 2, with water as a lubricant. Once the Discs 4, which have a sharp upper Edge 8B around their center Aperture 8, are forced on, they will become difficult to remove; since the sharp Upper Edge 8B will tend to dig deeper into the elastomer projection, rather than move off.

It is obvious in FIG. 1 that the only possible place for a hypodermic needle to penetrate, is through the elastomer projection. However, by choice of size, the Hole 8 in the impaled metal Disc 4 is approximately the same size as the smallest hypodermic needles. (i.e. approximately 0.026 inch in diameter) Therefore, it is impossible, without extraordinary force, to drive a Needle 7 through the Hole 8 and the Elastomer Projection 2; since there is no room for the projection to expand and accomodate the extra volume of the Needle 7. This situation is depicted in FIG. 2, where the parts that have been referred to are shown to scale.

FIG. 3A shows the basic elements of the armoring system as they would be layed out with the proportions and the measurements that have already been given; on a scale of ten to one. A small actual size matrix of just the elastomer projections is shown in FIG. 3B; to keep the diminutive nature of the armoring system in perspective. Further, with reference to FIG. 3A, it will be seen that the projections 2 are arranged in a plurality of parallel rows R1 and also in a plurality of parallel rows R2. The distance between adjacent projections in each row R1 and each row R2 is the same. The diameter of each disc is coordinated with the distance between each pair of adjacent projections so that the discs on any one projection overlap the discs on each adjacent projection.

FEATURES FOR AUTOMATIC ASSEMBLY

Several features of the basic design lend themselves to automatic assembly; without adhesives or fasteners, and without the kind of close tolerances that could make the automatic handling of such small parts very difficult.

Both the assembly and retention of the individual Armor Discs 2 makes use of a special property of some elastomers. On a short term basis, rubber-like materials may be squeezed or pinched by relatively sharp edges and bounce back without showing any particular signs of stress. However, when the sharp edges are allowed to remain in place for a length of time, the compressed elastomer will begin to cold flow around the high pressure points along sharp edges, making it virtually imposesible to move the sharp edged object along the surface of the elastomer. This characteristic is enhanced by the conic lower edge 8A and the sharp upper edge 8B of the Disc Aperture 8, to retain the Armor Discs 3 and 4, after they have been pressed on to the slightly oversized elastomer Projections 2, as shown in FIG. 1A.

Another characteristic of elastomers that becomes useful in assembly, is the elastomers preference for water as a lubricant; which can be used in the assembly process, without fear of residue or secondary effects of the elastomer.

FIG. 1A shows an enlarged representation of a single Elastomer Projection 2 and Armor Disc 3; with the cold flow of the elastomer over the upper and lower edges of the Disc Aperture 8. In addition, it can be readily seen how the design of the sharp "chisel like" upper edge of the Disc Aperture 8B will tend to hook into the elastomer projections when forcibly moved upward.

In FIG. 4 the edge of a scalpel Blade 10 is shown crossing the surface of the Armor Discs 3. It is obvious that the Blade 10 may cut through one or more of the elastomer Projections 2; however, the Blade 10 will not be able to penerate the Armor Discs 3; and the slicing of the elastomer Projections 2 will not cause release of the Armor Discs 3, or cause them to cease to function.

TOLERANCES

The basic design of the Armoring System provides for substantial tolerances for both the placement of the elastomer projections 2 and the size of the Armor Discs 3 and 4; which can be at least 5% of the dimensions used. This degree of worst case tolerance is depicted in FIG. #5, which shows the intercept point of each quad of discs, where the 5% tolerance could allow a 0.005 inch Space 11. A small 0.025 diameter hypodermic needle is shown in exact proportion, and in position to attempt a penetration between the stainless steel Discs 3 and 4, in the disc compliance Space 11. It is obvious that the needle could not penetrate to the hand of the wearer.

TRANSFERRING THE SENSE OF TOUCH

Figure 6:
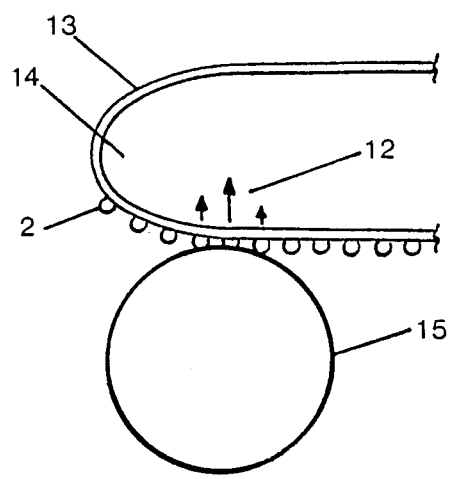
FIG. 6 shows a finger tip section of an armored glove; with a representation of the distribution of pressure to the finger tip through the individual projections, when contacting an external object.

FIG. 6 is a representation of a finger tip Section 13 of a rubber finger cover, which utilizes the invention; and which shows how the multiple Projections 2 transfer the Pressure Pattern 12 from a contacted Object 15 to the Finger 14 of the wearer—much the same as the braille system works for the blind. The individual elastomer Projections 2 are shown grossly oversize for clarity. Again refer to the actual size reference, shown in FIG. 3B.

A section of an armored Finger Cover 13 is shown, covering a Finger Tip 14; with a number of Projections 2 that are in contact with an external Object 15. The armor discs are not shown, and only the projections on the bottom of the finger tip are shown, for clarity. The non flat Object 15 will present a gradient of pressures to the matrix of Projections 2, which will, in turn, transfer the pressure points directly to the finger. Since there is more pressure per square inch on each of the individual projections than there would be on a flat surface, the pressure points tend to compensate for the loss in over all pressure through the elastomer Projections 1 and the apertures of the armor Discs 3 and 4.

Figure 7:
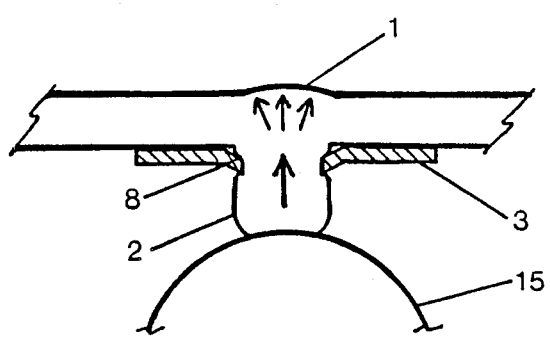
FIG. 7 shows an enlarged section of an individual elastomer projection, with pressure lines to indicate the distribution of pressure when being transferred through an armoring disc.

FIG. 7 shows a greatly enlarged single Projection 2 and associated Disc 3. The arrows designate the external pressure transfer from an individual Projection 2, as the pressure would be conducted through a Disc Aperture 8, and proceed to deform the inside surface of the basic elastomer Cover 1.

SUMMARY

The new armoring system invention provides a totally acceptable answer to the very important problem of protecting both surgeons and health workers from being unecessarily exposed to lethal viruses from accidental cuts and needle sticks, from scalpels and hypodermics needles. The methods for production of the invention are easily implemented with automated techniques; and, therefore, the invention can be made less expensive than those products that are labor intensive, such as chain mail gloves.

Gloves or full length finger cots that are designed with the new armoring method are made with a high temperature elastomer such as silicone; which enable the armoring units to be reused over and over again, after going through a cleaning and sterilizing process between usages.

I claim:
1. An armored cover comprising:
    a flat, flexible elastomer base having a plurality of identical, cylindrically shaped, spaced apart projections extending outwardly from at least one face of the base and arranged in a plurality of parallel rows;
    a plurality of identical discs made of metal and respectively disposed on said projections, the inside diameter of a disc being less than the outside diameter of its projection and conically shaped to develop forces to hold the disc on the projection; and
    the distance between any pair of adjacent projections in any row is the same and the outside diameter of each disc being chosen so that the disc on any one projection and the disc on any adjacent projection overlap each other.
2. The cover of claim 1 wherein:
    in each disc said conical shape has edges which are sharp and compress the projection on which the disc is mounted.

* * * * *